United States Patent [19]

Roberts

[11] Patent Number: 5,123,842
[45] Date of Patent: Jun. 23, 1992

[54] SINGLE TOOTH DENTAL IMPLANT METHOD

[76] Inventor: Ralph A. Roberts, 920 Rio Dell Ave., Rio Dell, Calif. 95562

[21] Appl. No.: 649,546

[22] Filed: Feb. 1, 1991

[51] Int. Cl.$^5$ .................... A61C 13/12; A61C 13/225; A61C 8/00
[52] U.S. Cl. .................................. 433/173; 433/172; 433/176
[58] Field of Search ................ 433/172, 173, 176, 215

[56] References Cited

U.S. PATENT DOCUMENTS

| | | | |
|---|---|---|---|
| 3,577,853 | 5/1971 | Roberts | 433/176 |
| 3,738,004 | 6/1973 | Edelman | 433/176 |
| 4,661,066 | 4/1987 | Linkow et al. | 433/176 |
| 4,693,686 | 9/1987 | Sendax | 433/173 |
| 4,799,886 | 1/1989 | Wimmer | 433/176 |
| 4,812,120 | 3/1989 | Flanagan et al. | 433/173 |

Primary Examiner—Gene Mancene
Assistant Examiner—Cindy A. Cherichetti
Attorney, Agent, or Firm—Eugene M. Eckelman

[57] ABSTRACT

An elongated flat body member has an implant end arranged to be embedded in the jaw bone and a post end arranged to project out of the jaw bone for support of a tooth crown. The post end of the body member has a lateral projection which serves as an abutment locator for a permanent crown mounted on the post end. The post end of the body member has a highly polished smooth surface area which forms a re-contouring portion for gum tissue as it heals around the body member. The implant end has a tapered shoulder and the polished area has tapered portions leading into these tapered shoulder portions of the implant end.

1 Claim, 1 Drawing Sheet

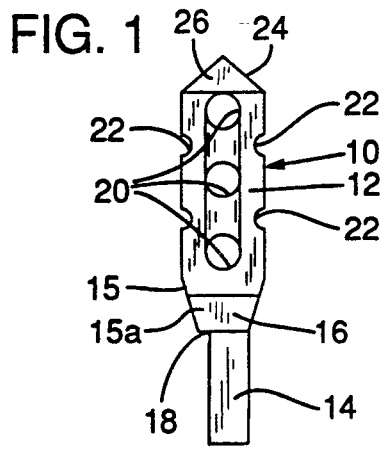
FIG. 1
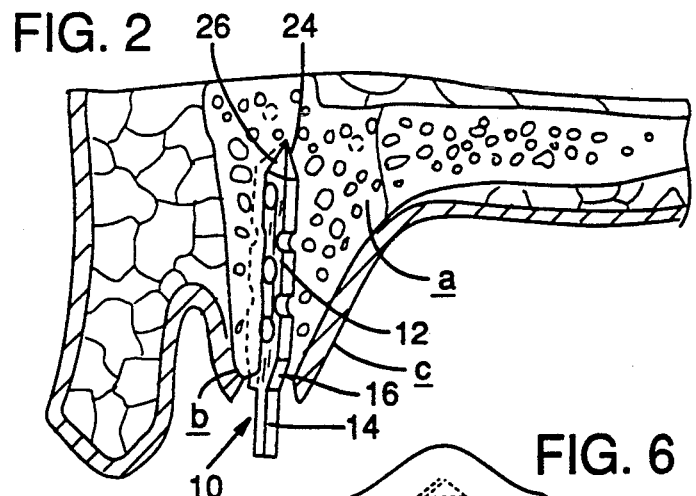
FIG. 2
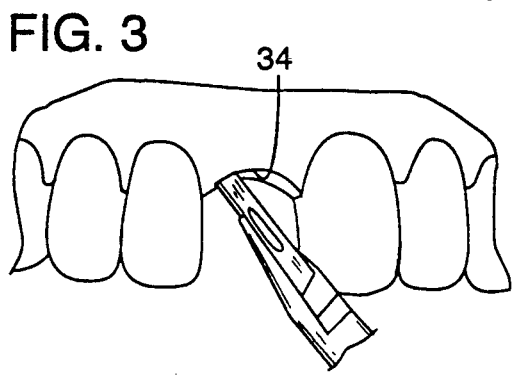
FIG. 3
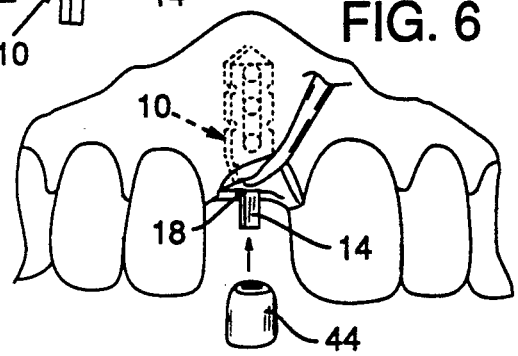
FIG. 6
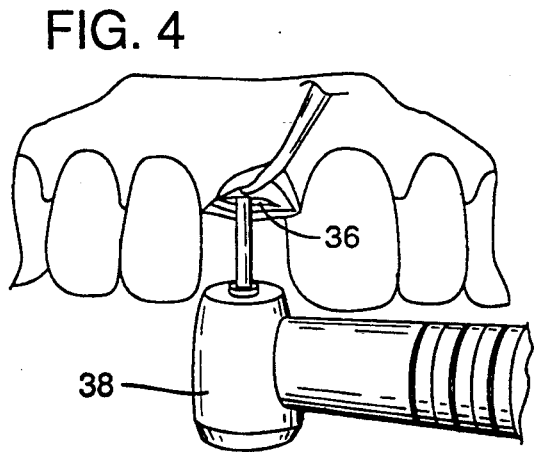
FIG. 4
FIG. 5
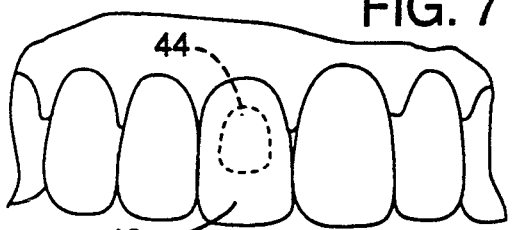
FIG. 7
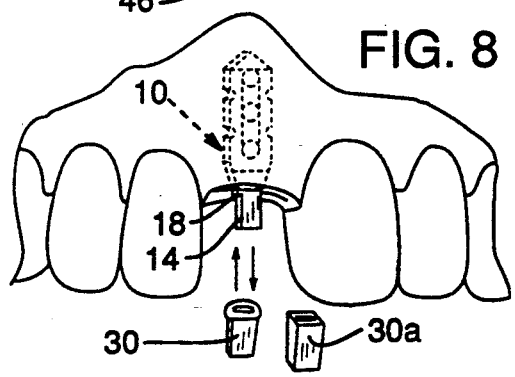
FIG. 8
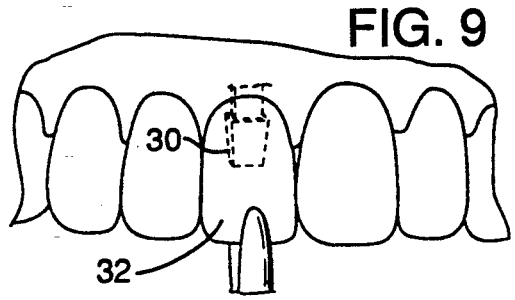
FIG. 9

SINGLE TOOTH DENTAL IMPLANT METHOD

BACKGROUND OF THE INVENTION

This invention relates to new and useful improvements in dental implants.

A need for an efficient single tooth replacement implant has long existed. That is, it is frequently necessary for the dentist to replace individual lost teeth. Currently a permanent or fixed bridge may be used where natural teeth are of a structure and arrangement to support such a bridge. Or, in other instances, removable bridges may be anchored to adjacent teeth. These bridges have certain disadvantages. For example, adjacent teeth must stand up under the forces imparted to them by the bridges and if not they are subject to damage. Also, some bridges require cumbersome appliances in the mouth. Further, food particles may accumulate in the areas between the bridge and the gum.

A single tooth replacement implant has been proposed heretofore as illustrated in U.S. Pat. No. 3,738,004. Such implant employs a complex base or implant portion that requires an overly large displacement area in the jaw bone. It thus has a disadvantage that it weakens the jaw bone and another disadvantage is that it is difficult to install and to properly position.

Ramus implants have also been proposed as illustrated in U.S. Pat. No. 3,577,853. This single post type implant finds efficient use for anchoring bridges to the ramus portion of the jaw bone. Due to their size and shape, however, they are not effective in other areas of the jaw bone and also are intended for use in the lower or mandibular bone only.

According to the present invention and forming a primary objective thereof, a single tooth replacement implant is provided that has substantial improvements and structure over prior implants and also accomplishes substantial improvements in the method of installation.

A more particular object is to provide a straight, one-piece, post-type implant that forms a good anchor for a tooth crown when installed, that can be installed by a simplified and fast procedure by skilled personnel, and that employs means facilitating accurate placement in the jaw bone as well as contributing efficiently to the healing process of the bone and gum and re-contouring of the gum tissue and papilla. Another object is to provide a single tooth replacement implant that can be used in substantially any area of the jaw bone, including replacement for centrals, laterals, cuspids and bicuspids, in both the upper and lower jaws.

In carrying out the objectives of the invention, the post-type implant comprises an elongated, flat body member having an implant end to be embedded in the jaw bone and a post end projecting out of the jaw bone on which a tooth crown is to be mounted. The implant end has a tapered shoulder portion that is embedded within the jaw bone adjacent the alveolar crest of the latter. The implant also has a polished neck and a seating ledge that are left exposed for tissue recontouring, the seating ledge providing for the proper seating of temporary and permanent crowns, respectively. The polished neck portion has edge tapers that lead into the tapered shoulder portion of the implant end. The permanent tooth crown is arranged for mounting on the post and positioned by the seating ledge for specific spacing from the jaw bone and gum to leave an area around the post for the recontouring of gum tissue. The implant portion includes a plurality of holes and/or notches for receiving bone growth. The polished portion of the post forms an efficient recontouring surface for the gum tissue. The permanent crown is associated with a permanent crown base that is secured to the implant post portion. This crown base is arranged to be shaped on its exterior surface for securement to the permanent crown. In the process of replacing a removed tooth, the implant portion of the flat body member is installed in the jaw bone with the post portion thereof projecting and its seating ledge selectively spaced from the jaw bone. The crown base is permanently mounted on the post portion of the blade in abutment with the seating ledge whereby to leave an area around the post portion for the recontouring of the gum tissue between the tooth crown and the jaw bone. The seating ledge preferably comprises a lateral projection which serves as an abutment, and this lateral projection can be ground away a selected amount if necessary to provide the proper spacing of the tooth crown from the jaw bone.

The invention will be better understood and additional objects and advantages will become apparent from the following description taken in connection with the accompanying drawings.

BRIEF DESCRIPTION OF THE DRAWINGS

FIG. 1 is an elevational view of a single tooth replacement implant of the instant invention.

FIG. 2 is a sectional view of a jaw bone or alveolus with the present implant secured therein, the implant being viewed isometrically for clarity.

FIGS. 3, 4 and 5 are perspective views showing surgical steps of preparing gum tissue and jaw bone for receiving the implant.

FIG. 6 is a perspective view showing a step in the process wherein the implant has been inserted in the jaw bone with a post portion projecting, and also showing a temporary crown base in the process of being installed on the projecting post.

FIG. 7 is a perspective view showing a step in the process wherein a temporary crown is installed on the temporary crown base.

FIG. 8 is a perspective view showing a step in the process wherein the temporary crown and its base have been removed and a permanent crown base is to be mounted on the projecting portion of the post, this view showing a finished and rough blank form of the permanent crown base, and FIG. 9 is a perspective view showing the completed single tooth replacement, the implant portion and the permanent crown base being shown in broken lines.

DETAILED DESCRIPTION OF A PREFERRED EMBODIMENT

With particular reference to the drawings and first to FIG. 2, the present single tooth implant 10 is arranged to be embedded in a jaw bone a. This illustration shows the implant in the upper jaw bone but it can be installed in either the upper or lower one. In FIG. 2, b represents the alveolar ridge of the jaw bone, and c represents gum tissue. The single tooth implant 10 of the instant invention comprises a flat bar-like member having a bone engaging or implant end 12, also seen in FIG. 1, a projecting post end 14 for supporting a crown thereon, and tapered side edge shoulders 15 between the implant end and the post end. Shoulders 15 taper from the outer end of implant end 12 and lead into tapered side edge portions 15a of a highly polished portion 16 on the post end 14. This polished portion will be mostly exposed when the implant is inserted in the jaw bone. One side edge of the implant has a seating ledge 18 or abutment 18 at the outer end of the polished portion. The body portion 12 has apertures 20 along its longitudinal center through which bone grows for positively anchoring the implant in place. Side notches 22 are also provided in the edges of the body portion 12 for additional anchored securement to the jaw bone by bone growth. The inner end of the implant has end tapers 24 leading from opposite side edges as well as tapers 26 leading from the opposite faces. The implant is thus sharpened at this leading end for forced penetration into the jaw bone as will become more apparent hereinafter.

The length of the body portion 12 may vary depending upon the height of bone in which the implant is to be placed. The number of apertures 20 and side notches 22 will vary according to the length of the body portion. Representative lengths of the body portion are 12 mm, 15 mm, and 18 mm. The length of the post portion 14 is 8 mm for all sizes. The width of the implant is approximately 5 mm and its thickness is approximately 2 mm. The highly polished area 16 is approximately 3 mm in its height. Area 16 comprises a healing and re-contouring area of the gum tissue and papilla after the implant is installed. The smooth surface achieved by the polished surfaces enhances gum re-contouring. The dimensions as set forth may of course vary a small amount.

With reference to FIGS. 8 and 9, the invention also include, a crown base or coping 30 that is installed permanently on the post and forms an anchored connection between the implant and a permanent crown 32. Permanent crown base 30 may initially comprise an unfinished blank form 30a that is secured to the post and then prepared by reduction to the proper shape 30 as one would reduce a natural tooth, or the crown base 30 can be initially molded to shape and then merely secured into place on the post. The crown 32 is prepared and mounted on the crown base in the same manner that a crown is prepared and mounted on a reduced natural tooth.

Seating ledge 18 on the post 14 serves as an abutment for positioning the permanent crown base 30 on the post, thus ensuring proper spacing of this base relative to the alveolar ridge of the jaw bone. If there is a need to seat the crown base deeper, the seating ledge 18 can be ground down.

In the process of installing the present implant, and with reference to FIG. 3, an incision 34 is first made in the gum tissue in the area which is to receive the implant to reflect just enough of the jaw bone to visualize a width and angulation thereof. Thereupon, as shown in FIG. 4 an opening 36 is made in the surface of the jaw bone by a suitable surgical burr 38 for receiving one or more bone spreading instruments 40, FIG. 5. After such initial opening is made, these bone spreading instruments are forced into the jaw bone in progressive sizes to form a recepter sight for the implant 10. The implant 10, FIG. 6, is then forced into place in known procedures, and according to the present invention, it is installed such that unpolished portion of the shoulder 15 is embedded in the bone and the polished portion 16 and the seating ledge 18 will be exposed. The polished portion will allow the soft tissue of the gums to form a cuff around the post. Sutures are then applied to close the incision.

Thereupon, a temporary crown base 44, FIG. 6, in the shape of a cap is mounted on the post portion 14 of the implant and a temporary crown 46, FIG. 7, is formed therearound in a conventional manner. After a 3 month healing process of the bone, the temporary crown 46 and its base 44 are removed and a permanent crown base 30 or 30a is installed on the implant post portion 14. With either of these two forms, they are abutted against the seating ledge 18 for proper spacing from the crest of the jaw bone. If desired or necessary, the seating ledge 18 may be ground away as stated hereinbefore for proper spacing of the crown base. The attachment of the crown base 30 or 30a to the post portion 14 is a permanent attachment, and the final step comprises forming or attaching the permanent tooth crown 32 to this base in a conventional manner.

It is to be understood that the form of my invention herein shown and described is to be taken as a preferred example of the same and that various changes in the shape, size and arrangement of parts may be resorted to without departing from the spirit of my invention, or the scope of the subjoined claims.

Having thus described my invention, I claim:

1. A process of installing an artificial tooth in a person's mouth to take the place of a tooth that has been removed, comprising the steps of providing an initial depth opening in the surface of the jaw bone at the location at which an artificial tooth is to be installed, deepening the opening in the jaw bone from said initial opening by forcing progressively larger bone spreading instruments thereinto until a size of opening is made that will receive an implant portion of an artificial tooth in a forced fit, and then forcing the implant portion of the artificial tooth into the prepared opening to provide positioning of the implant for bone growth securement thereto.

* * * * *